United States Patent [19]
Larsen et al.

[11] Patent Number: 5,922,443
[45] Date of Patent: Jul. 13, 1999

[54] POLYMERIC ARTICLE, SUCH AS A MEDICAL CATHETER, AND METHOD FOR MAKING THE SAME

[76] Inventors: Charles E. Larsen, P.O. Box 5149, Aguadilla, Puerto Rico 00605; Leonard Pinchuk, 9834 SW. 111 Ter., Miami, Fla. 33176; Thomas D. Weldon, P.O. Box 5149, Aguadilla, Puerto Rico 00605

[21] Appl. No.: 08/485,342

[22] Filed: Jun. 7, 1995

Related U.S. Application Data

[62] Division of application No. 08/074,270, Jun. 8, 1993., Pat. No. 5,484,565, which is a continuation of application No. 07/703,486, May 21, 1991., abandoned

[51] Int. Cl.⁶ .............................. B32B 7/02; B32B 27/34
[52] U.S. Cl. .................. 428/217; 428/423.1; 428/423.3; 428/474.4; 428/475.5
[58] Field of Search .............................. 427/2.3, 322, 336; 428/217, 423.1, 423.3, 474.4, 474.9, 475.5

[56] References Cited

FOREIGN PATENT DOCUMENTS 1-17384  3/1989  Japan .

*Primary Examiner*—D. S. Nakarani
*Attorney, Agent, or Firm*—Kenyon & Kenyon

[57] ABSTRACT

A polymeric article and method for making a polymeric article, such as a catheter, are disclosed wherein the article is contacted with a swelling agent, such as a solvent, and a plasticizer to make the polymeric material softer and/or more pliable or flexible. The contacting may be carried our sequentially or simultaneously, using a solution containing a plasticizer and a solvent.

4 Claims, 5 Drawing Sheets

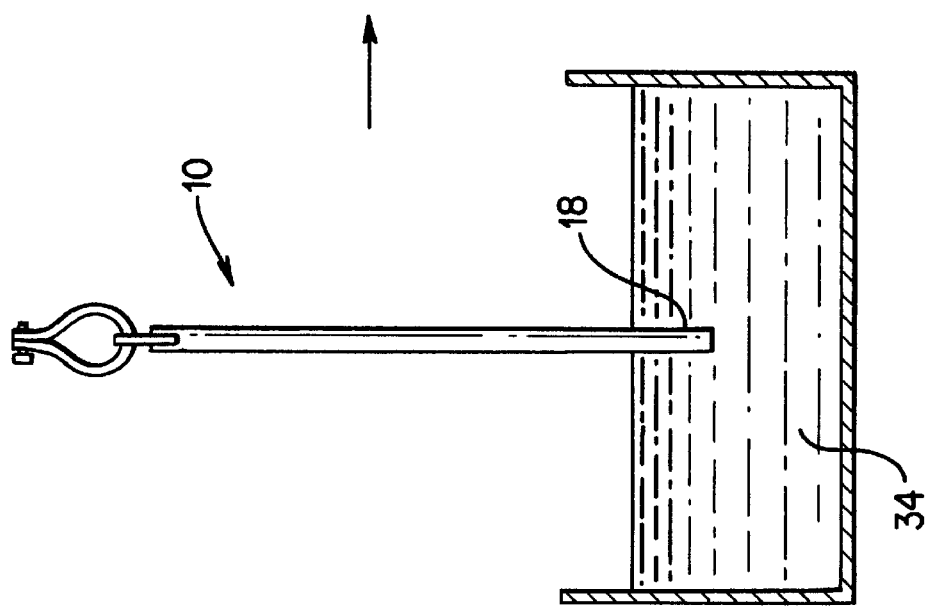
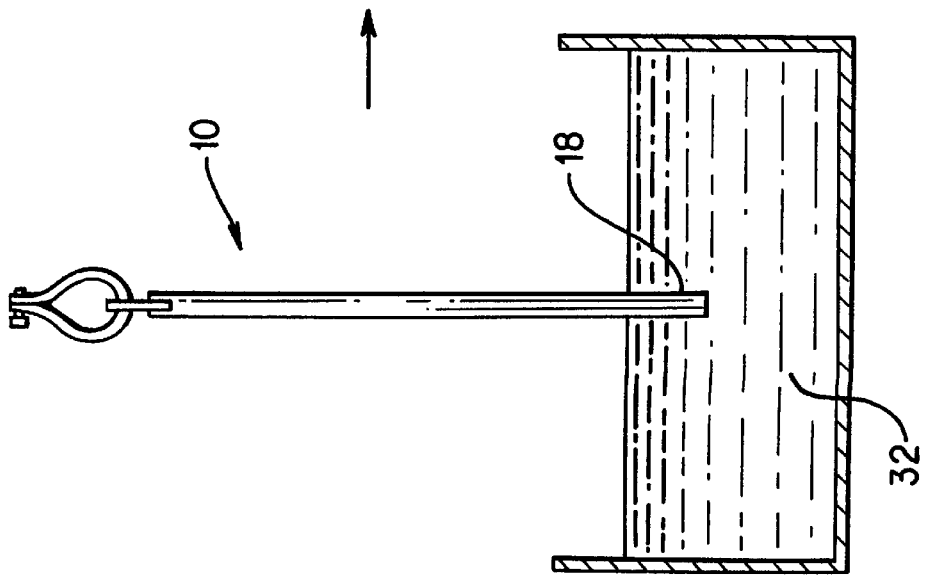

POLYMERIC ARTICLE, SUCH AS A MEDICAL CATHETER, AND METHOD FOR MAKING THE SAME

This application is a division of application Ser. No. 08/074,270, filed on Jun. 8, 1993, now U.S. Pat. No. 5,484,565; which is a continuation of application Ser. No. 07/703,486 filed on May 21, 1991 now abandoned.

BACKGROUND OF THE INVENTION

The present invention relates to articles of softened polymeric material and/or articles of polymeric material which have portions of differing softness, pliability or flexibility, and to a method for making such articles. More particularly, this invention relates to medical catheters, such as thin-walled angiographic catheters, guiding catheters, angioplasty catheters, urinary tract catheters, gastroenterology catheters, and the like, and to a method for making such catheters wherein the catheter includes an elongated body or shaft portion and a softer or more pliable or flexible distal end portion which is integral to its adjacent shaft portion. Even more specifically, this invention relates to a three zone catheter that includes 1) a relatively stiffer body portion, 2) a softer, or more pliable or flexible distal end portion which may terminate in 3) an even softer or more pliable or flexible tip end portion.

Catheters are widely used in the medical field for a variety of applications, including both diagnostic and therapeutic procedures. Depending on the particular medical application, it is often desirable for different parts of the catheter to exhibit different physical characteristics. For example, radiological catheters are widely used in angiographic applications where it is necessary to administer a fluid at a location within the cardiovascular system of a patient. Because these catheters are inserted into and passed through the blood vessels of the vascular system, they necessarily must have a very small outside diameter. On the other hand, because the radiologist usually desires to administer large boluses of radiopaque dyes or the like at high flow rates to obtain the sharpest x-ray image, the catheter lumen should have the largest possible inside diameter (i.e., the catheter should have the thinnest possible wall). However, competing considerations which limit the thinness of the catheter wall are the need for high strength to withstand the high pressures of liquid injection, which may exceed 1000 psi, and the need for a high degree of tensile strength and stiffness in order to allow the catheter to be pushed, guided and manipulated through the vascular system of the patient without kinking or buckling. Accordingly, in addition to being thin-walled, catheters such as angiographic catheters should have a shaft or body portion with good mechanical stability, burst strength and kink resistance.

Yet, it is often desirable for the same catheter to have a more pliable distal end portion. For example, many specialty catheters such as diagnostic catheters and urinary stent catheters are shaped at a distal end portion into specific configurations to reach difficult vessels and/or to locate a portion of the catheter within the various vessels, sinuses and cavities. The distal end portion of a so-called Judkins catheter, as an example, is bent into a bell-like shape to help insert the tip into the coronary arteries. The distal end portion of a coronary diagnostic catheter is typically formed into a pig-tail or loop to allow lodgement of the catheter tip in the heart ventricles. Similarly, a urinary stent may utilize a double pig-tail, i.e., one on each end to allow lodgement of the catheter tips in the kidney calyxes as well as the urinary bladder. Because many of these catheters are inserted into the patient along and over guide wires, it is desirable for this bent or formed portion to be more flexible or pliable than the body portion of the catheter to enable sliding of the catheter over the guidewire without significantly distorting the guidewire.

Further, because catheters typically must be able to reach distant vessels within the body without damaging, tearing or causing trauma to the various tissue, the tip end portion of the catheter is preferably even softer and less traumatic than the body and adjacent portion of the distal end of the catheter. Unless the context indicates otherwise, for purposes of this description "distal end" means generally the portion or area at the end of the catheter which is located farthest from the physician or other medical personnel using the catheter. The term "mid-distal end" is used herein with reference to a part of the distal end portion which does not extend to the very tip end of the catheter. "Tip end" is used herein to refer to the most distal end portion of the catheter. For example, an angiographic catheter of the type which must be passed through blood vessels and/or into the ostium of a coronary artery should not cause trauma to the lining of the vessel or to other tissue, such as a heart leaflet valve. Accordingly, in order to reduce the risk of trauma, it is desirable that such a catheter, while having a body and/or mid-distal end portions which meet the above criteria, also have an even softer or more flexible tip or tip end portion.

The prior art has attempted in several different ways to address the need for a catheter which has different portions exhibiting different characteristics. As described, for example in U.S. Pat. No. 4,551,292, a catheter with a more rigid body and a softer tip may be provided by separately molding the body portion and the distal or tip portion of different materials and joining them by either heat sealing, sonic sealing, solvent bonding or other fusing techniques.

One drawback with such a "two-piece" or "three-piece" catheter, however, is the possibility that the distal or tip end may separate from the body of the catheter during a medical procedure. Fused multi-piece catheters have an abrupt transition from the harder portion end to the fused-on softer portion. This abrupt transition focuses stresses on the fuse joint which renders it more susceptible to kinking and further risks separation. Regardless of the medical procedure, inadvertent separation of the distal or tip end from the catheter body or shaft during the procedure is to be avoided. With vascular catheters such as angiographic catheters which are used in cardiovascular procedures and are often used in close proximity to the heart, separation can create risk of serious harm to the patient. For example, a separated catheter may reduce blood flow to the heart or actually lodge within the heart and require immediate surgery to remove. In the best of circumstances, a separated end is a great inconvenience for the surgeon and, at worst, is life-threatening and possibly fatal to the patient.

Unfortunately, the potential for end separation is increased in thin wall catheters, such as angiographic catheters or guiding catheters, where the reduced wall thickness may not provide a sufficient amount of cross-sectional area to allow for the secure attachment of the distal or tip end portion of the catheter to the catheter body or shaft. For similar reasons, thin wall catheters of two-piece or three-piece construction require more precise, laborious and time-consuming assembly techniques and test procedures to better insure the security of the bond between the end and shaft and to provide smooth, continuous and confluent inner and outer walls of the catheter to prevent snagging of the catheter within a guiding catheter or of a guidewire within a catheter lumen. Finally, fused-multi-piece construction makes assembly of multilumen catheters extremely difficult.

Accordingly, the prior art also discloses several efforts to provide a catheter having a softer end portion but wherein the end portion is of a one-piece or fuseless construction with the body portion of the catheter. For example, U.S. Pat. No. 4,753,765 describes a catheter having a two-layered tubular body portion with a rigid inner sheath and a more flexible outer sheath. The end portion is an integral extension of the flexible outer sheath that is co-extruded over the rigid inner sheath and extends beyond the distal end of the inner sheath.

The precision co-extrusion process described in U.S. Pat. No. 4,753,765, however, has many drawbacks. One drawback is that the extrusion is difficult to control, particularly for thin wall catheters, as it utilizes an underlying material having a significantly higher melting point than the top extruded material. This dissimilarity of materials may also adversely affect bonding. Another drawback is that thin tubes require a wire mandrel support for the tubing which can be quite costly. Also, the process described in U.S. Pat. No. 4,753,765 is not conducive to mass production because the underlying sheath is discontinuous, and this may also significantly increase the expense of manufacturing these catheters. Another drawback with this type of catheter is the abrupt transition between the hard and soft sheaths. Finally, the requirement for multiple layers, in particular for a three zone catheter (having a body or shaft portion of certain hardness and a softer mid-distal end portion and an even softer tip end portion), may increase the overall outside diameter of the catheter and/or reduce the diameter of the lumen, both of which are to be avoided.

The prior art also discloses a catheter body and tip of relatively soft material, with braiding provided along the body portion to provide the desired stiffness and burst resistance. Braiding a thin wall catheter, however, is a difficult and expensive process which results in greater waste, higher than desirable wall thicknesses, and increased costs. Moreover, braiding a three zone catheter is even more difficult and costly to perform.

Another prior art patent, U.S. Pat. No. 4,960,410, describes a two piece construction having a helix cut through the wall of the distal tip of the catheter to provide flexibility and pushability. The portion is then sheathed with a thin softer tube to complete the catheter wall. One drawback with this catheter and method for making such a catheter is that cutting the helix, sheathing and bonding the sheath to the inner catheter is both laborious and costly. In addition, although this construction provides a pliable or flexible distal zone, it does not provide a softer end or tip portion that is atraumatic to the blood vessel lining.

Another technique for forming a fuseless catheter of differing characteristics is described in U.S. Pat. No. 4,963, 306. This patent discloses a novel method of making a fuseless, thin-walled catheter without co-extruding multiple layers of plastic, braiding or bonding a separate tip. In general, the method includes subjecting the body or shaft portion of an extruded polymeric tube of the catheter to solid state polymerization, while shielding or excluding the distal portion from the solid state polymerization process. The effect of the solid state polymerization process is to make the body or shaft portion of the catheter harder and more rigid. The distal portion, however, in which solid state polymerization has been retarded, remains softer and more pliable. Accordingly, although solid state polymerization effectively hardens a polymer and can be used to harden the body portion of a catheter relative to the distal portion, it cannot be used to soften an existing polymer or catheter tube, for example, for making the very tip end of an existing catheter tube even softer and atraumatic.

Still another prior art patent, Japanese Patent No. 1-17384, describes an integral soft-tip catheter made by dipping the leading edge of the catheter into a solution of a plasticizer dissolved in a solvent that is a good solvent for the plasticizer but a "poor" solvent for the polymer comprising the catheter. A "poor" solvent for the polymer is identified as a solvent that will not cause the polymer to swell or otherwise adversely effect the polymer comprising the catheter.

Unfortunately, the method described in Japanese Patent No. 1-17384 requires a substantial amount of time (approximately four hours for thin-walled catheters) to even minimally plasticize the intended flexible portion. Further, this method limits the plasticizer that can enter the polymer to relatively small mobile molecules of the plasticizer. When the catheter is used, these smaller molecules can also more easily migrate out of the catheter and increase the possible risk of adverse tissue reactions. The higher molecular weight, low mobility plasticizers such as hexylbenzenesulfonamide are not readily imbibed or absorbed in sufficiently substantial amounts into the polymer system with these solvents.

Finally, the process described in Japanese Patent No. 1-17384, utilizing a "poor" solvent, does not permit the desired amount of plasticizer, typically approximately 25% by weight, to be absorbed into the polymer for a particularly soft tip. Thus, while the amount of plasticizer absorbed may be sufficient to somewhat reduce the bending moment or increase the flexibility of the distal portion of a catheter, it is insufficient to provide a distal tip end of a catheter which is particularly soft so as to further minimize the risk of trauma to the lining of blood vessels and/or tissue.

SUMMARY OF THE INVENTION

In general, the present invention is directed to an article of polymeric material which is softened, in whole or in part, after formation and, more particularly, to an article of polymeric material having portions of differing softness, pliability or flexibility, and to a method for making such an article by contacting the article or a portion of the article with a swelling agent to swell the material and with a plasticizer to allow for the migration or absorption of the plasticizer into the polymer.

The article may be contacted by the swelling agent and plasticizer in different ways, but is preferably contacted by immersion, such as by dipping, of the article or desired portion of the article into the swelling agent and plasticizer. Although the article may be contacted with the swelling agent and plasticizer sequentially, it is further preferred to immerse the article or the desired portion of the article in a solution which contains both the swelling agent and the plasticizer.

In contrast to the prior art, this method provides for substantial absorption of plasticizer into the polymer, including higher molecular weight and lower mobility plasticizers such as N-hexylbenzenesulfonamide, resulting in a particularly soft and pliable article or portion, with lower risk of subsequent migration of the plasticizer from the polymer.

In accordance with further aspects of the present invention, the swelling agent is an agent which will cause the polymeric material to expand without significant deleterious affect to the polymer. Preferably, the swelling agent is a solvent for the polymer and the plasticizer, used at a temperature sufficiently low and for a contact time period sufficiently short so as to not dissolve the polymer. Further, the solvent is preferably compatible with the plasticizer to provide a combined solution that allows the contacting step to be carried out simultaneously by dipping into the solution. The use of a solution of plasticizer and swelling agent acts synergistically to further increase the absorption of plasticizer into the polymer as compared, for example, to a sequential contacting process.

In accordance with further details of the present invention, the solution of plasticizer and solvent comprises about 10%–98% solvent and 2%–90% plasticizer and, more preferably, about 50%–90% solvent and about 10%–50% plasticizer. For a polyamide or polyurethane polymeric material, the preferred plasticizer is N-butylbenzenesulfonamide or N-hexylbenzenesulfonamide and, most preferably, the former. For polyamide material the preferred swelling agent is formic acid, and for polyurethane material, the preferred swelling agent is methylene chloride.

After the step of contacting, the residual swelling agent on or in the polymeric material is neutralized. This may be achieved by air drying or by contacting the article with neutralizing agent, such as by dipping the article into an alkaline liquid, e.g., a solution of ammonia. After neutralizing, thermoforming, grinding or other steps may also be used to form the article into the desired size and shape.

As noted above, the present invention has particular application in the manufacture of medical catheters having portions of differing softness or flexibility and, in particular, the manufacture of three zone medical catheters of the type having a shaft or body portion of certain hardness, a softer mid-distal portion and an even softer tip end portion. The method includes providing an elongated tube of a polymeric material having a lumen within, and contacting an end portion with a swelling agent to swell the polymer and a plasticizer to allow migration of the plasticizer into the polymer.

As described above, the end portion of the catheter may be contacted with the swelling agent and/or plasticizer in various different ways without departing from the present invention. However, the end portion of the catheter is preferably contacted by dipping it into a solution of the swelling agent and the plasticizer.

The swelling agent, plasticizer and solution are generally as summarized above. For the manufacture of medical catheters the end portion is preferably contacted with the solution for about 1–30 minutes, with such time being variable depending on, inter alia, the thickness of the catheter, the quantity and strength of solvent and plasticizer in the solution, and the temperature of the solution. For making a catheter having more than one portion of differing softness, an end portion of the catheter, e.g., the distal end portion, may be dipped into the solution for a selected period of time and then partially withdrawn, leaving the remainder, e.g., the tip end portion, in the solution for a longer period of time, resulting in portions of differing softness.

BRIEF DESCRIPTION OF THE DRAWINGS

FIG. 4 are elevation views of different steps of carrying out the method of making a catheter in accordance with another aspect of the present invention;

DETAILED DESCRIPTION OF THE DRAWINGS

The present invention is directed to an article of polymeric material and to a method of making a polymeric article, such as catheter, wherein the entire article or a portion of the article can be made softer and more flexible or pliable. Although the following detailed description of the preferred embodiment concerns a fuseless three-zone thin-walled angiographic catheter and the method of making such a catheter, it should be understood that the present invention is not limited to catheters in general or to three-zone angiographic or fuseless catheters in particular. The present invention may be used for other polymeric articles, such as catheter balloons or other articles, as well as for catheters in general, including, guiding catheters, angioplasty catheters, urinary tract catheters, gastroenterology catheters, and the like having or requiring two or more portions of different softness or flexibility.

Figure 1:
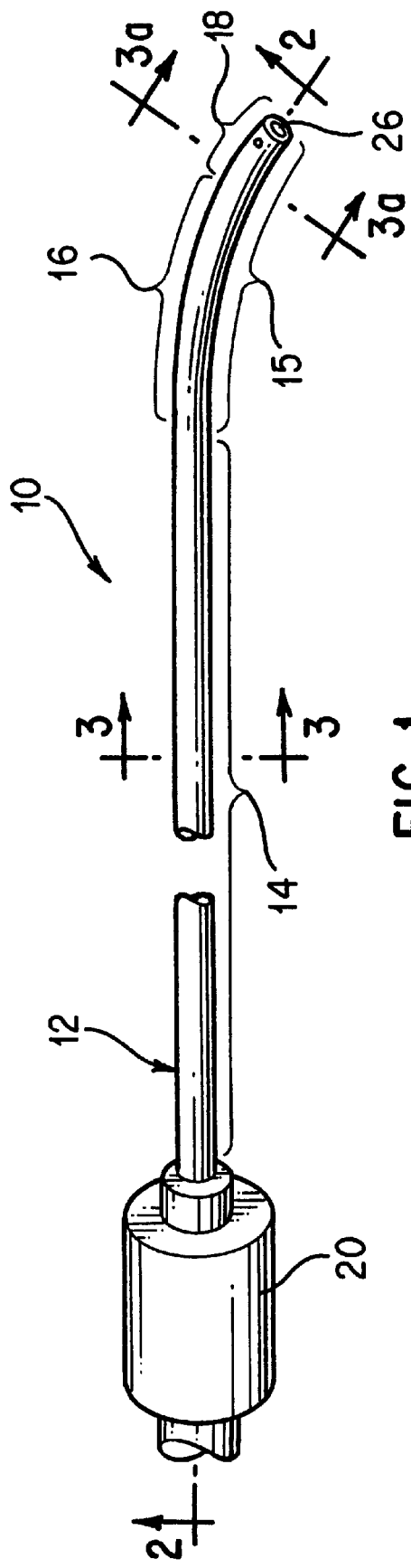
FIG. 1 is a perspective view, partially broken away, of an assembled angiographic catheter according to the present invention.

Turning to the attached drawings, the depicted catheter and the method for making it will be described generally before turning to more detailed aspects of the catheter and method. FIG. 1 depicts a three-zone angiographic catheter 10 which includes an elongated, fuseless polymeric tube generally at 12 having a body or shaft portion 14, a generally distal end portion 15, a mid-distal end portion 16, and an atraumatic tip end portion 18 at the most distal portion of the tube. A hub member 20 is secured to the proximal end of tube 12.

Figure 2:
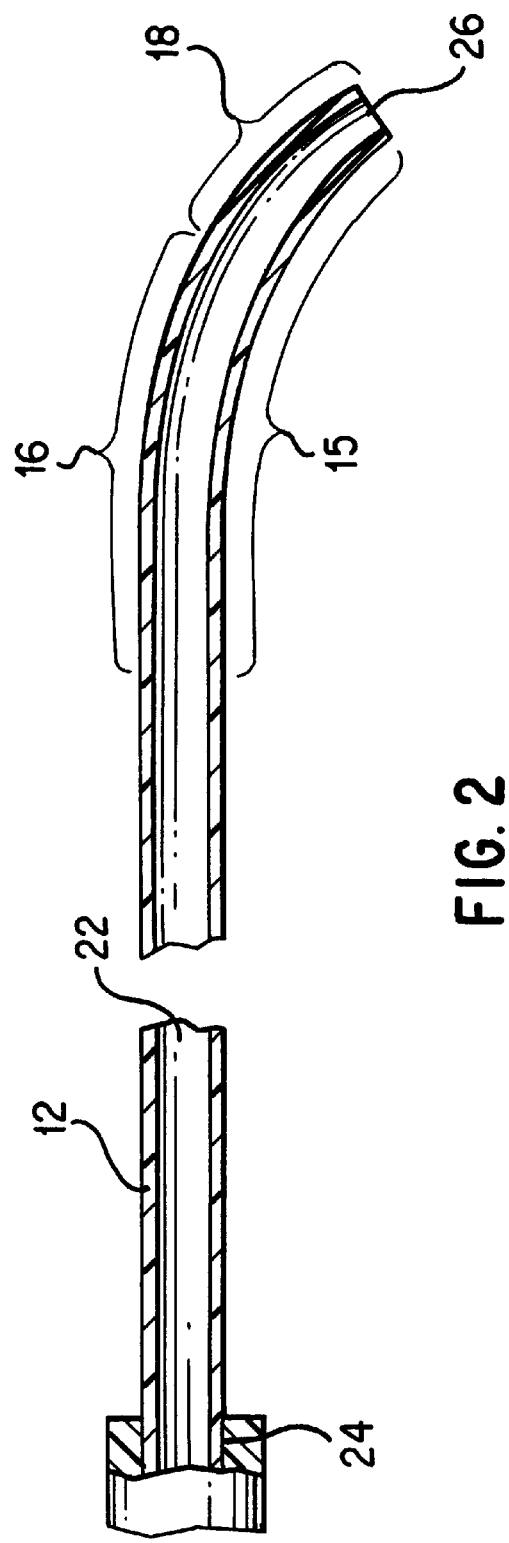
FIG. 2 is a longitudinal, cross-sectional view along line 2—2 of FIG. 1.

As seen in FIG. 2, a longitudinal lumen 22 extends through the elongated fuseless polymeric tube 12 from a generally coaxial bore 24 in the hub member 20 through the body portion 14, the mid-distal end portion 16, and tip end portion 18, terminating at end orifice 26 within the tip end portion.

Although depicted with a single lumen, the present invention is also applicable to catheters having a plurality of lumen, e.g., a fluid flow or instrument insertion lumen and an inflation lumen for inflating a balloon associated with the catheter. The tip end portion 18 may be mechanically tapered, ground or manicured such that the wall thickness at distal tip end portion 18 may be less than the wall thickness in mid-distal end portion 16 or body portion 14. Similarly, the inner lumen diameter at distal orifice 26 may be thermoformed to a diameter less than that of lumen diameter 22 at middistal end portion 16 and body portion 14, as is frequently encountered in catheter designs.

The elongated fuseless polymeric tube 12, including the body portion 14, the mid-distal end portion 16 and the tip end portion 18, may be constructed of a unitary sheath or cylinder which has been extruded in a single pass out of a precision extrusion device, although other techniques, such as injection molding, may also be used to form the tube. As shown in FIGS. 1 and 2, tip end portion 18 is preferably of one-piece, integral, fuseless construction with the mid-distal end portion 16 and catheter body 14. Alternatively, the mid-distal end portion 16 and tip end portion 18 may be of one-piece construction and fused to catheter body 14 by the use of heat, solvent, sonic or radio frequency energy or other suitable bonding method.

Figure 6:
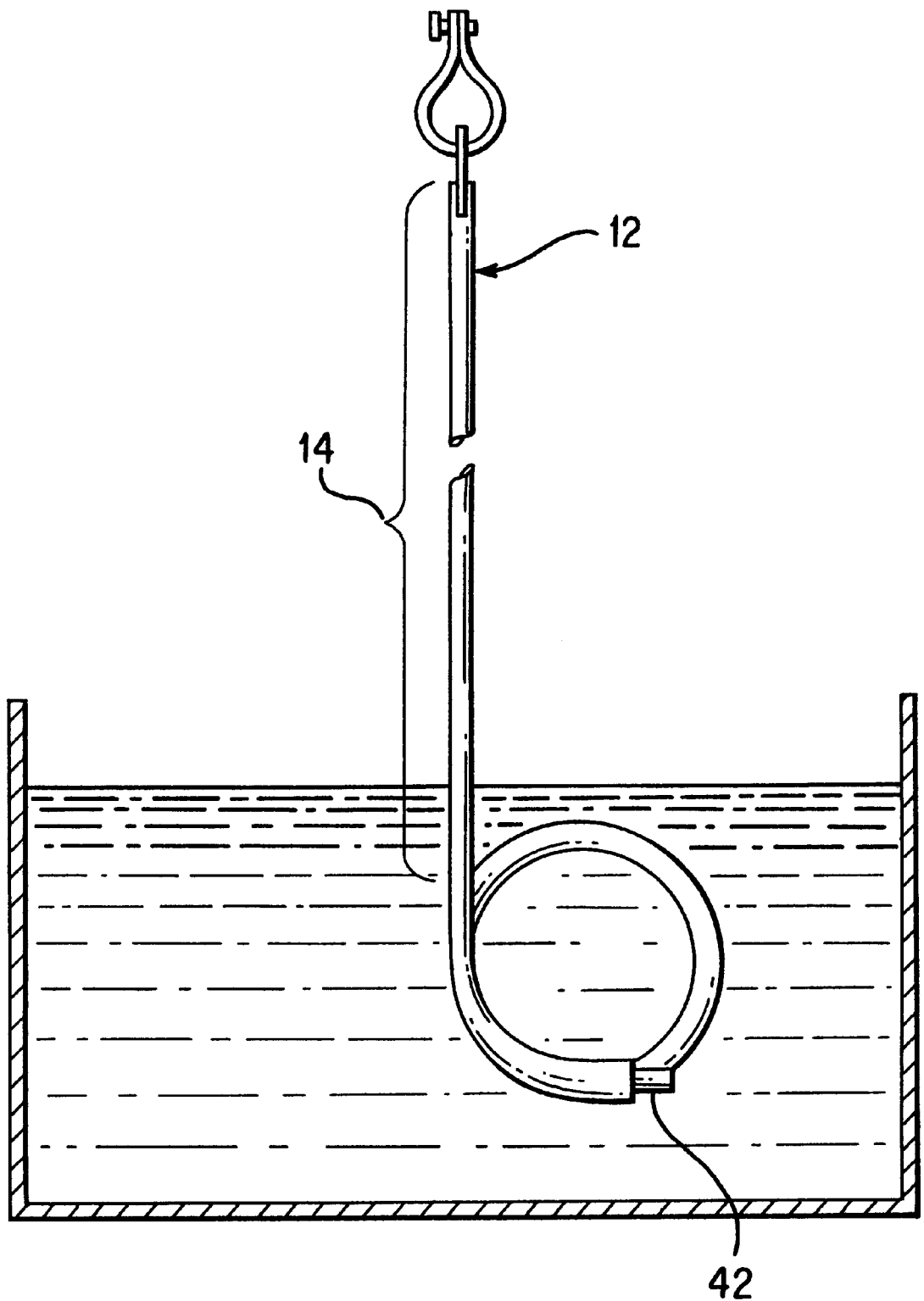
FIG. 6 shows another step, the forming of a pigtail shape on the distal end of the catheter, which may be employed in the method of the present invention.

Mid-distal end portion 16, and tip end portion 18, may have any of a variety of configurations, depending upon the medical procedure to be performed, without departing from the present invention. For example, the distal end portion 15 may exhibit a selected degree of curvature depending on the particular procedure in which the catheter is to be used. An example of this is shown in FIG. 6, which depicts a so-called "pig tail" distal section often used in catheters which must pass through a valve of a human heart. Further, as noted above, the tip end portion 18 may exhibit a gradual tapering of the outside diameter which decreases toward the distal orifice 26 or the inside diameter at distal lumen 22 may be smaller than the lumen diameter at mid distal end portion 16.

With reference to FIG. 3, a one piece, fuseless catheter, according to the present invention is manufactured by first extruding a tube of a polymeric material onto an air mandrel, a wire mandrel or other means, typically by utilizing a conventional wire coating extrusion apparatus in order to form a continuous cylindrical extrusion. The extruded tube is cut to the desired length for the elongated fuseless polymeric tube or catheter, and the mandrel (if a solid one is used) is removed. The elongated tube 12 is then placed on a stiff wire support mandrel or the like.

The portion of the tube that is to form the body portion 14 of the elongated fuseless polymeric tube 12 or catheter is preferably exposed to a high temperature zone as part of a solid state polymerization process described in detail in U.S. Pat. No. 4,963,306 which is incorporated by reference herein in its entirety. The distal end portion 15, including mid-distal end portion 16 and tip end portion 18 of the tube may be exposed to the solid state polymerization, but, as described in the above-identified patent, preferably is protected or shielded from the solid state polymerization process, thus rendering the mid-distal portion 16 and tip portion 18 more flexible than body portion 14.

Although the process described in U.S. Pat. No. 4,963,306 results in a catheter having a more pliable middistal end portion 16 and tip end portion 18, in accordance with the present invention, the tip end portion 18 of the polymeric tube 12 is made even softer and more pliable than the mid-distal portion 16 and considerably softer than catheter body 14 as a result of the addition of plasticizer to the tip portion 18 following extrusion (or other formation) of the tube 12.

In general, the plasticizer is added to the polymeric material of the catheter by contacting the tip end portion 18 with a solution including a swelling agent selected for the particular polymeric material used in making the catheter and a plasticizer also compatible with the polymeric material and, preferably, compatible with said swelling agent. The swelling agent temporarily causes the polymeric material of the tube to swell or expand, allowing the plasticizer to enter or migrate into the expanded polymeric material. The catheter may be contacted with swelling agent and plasticizer by spraying, wiping, immersing, dipping or other means, although immersion by dipping is the preferred method for contacting the swelling agent and plasticizer. Although the swelling agent referred to herein is preferably a liquid, it is also within the scope of the present invention to use other types of swelling agents which may now exist or later become known which are not liquid. However, one further advantage of a liquid solvent which is compatible with the plasticizer is that when used in solution with the plasticizer, the swelling agent also may act as a carrier to further help the plasticizer enter the polymeric material. The introduction of a plasticizer into the tip portion 18 of the tube 12 gives the tip portion 18 a degree of pliability, softness or flexibility greater than the body portions 14 and mid-distal section 16 which may or may not contain a plasticizer.

Figure 3A:
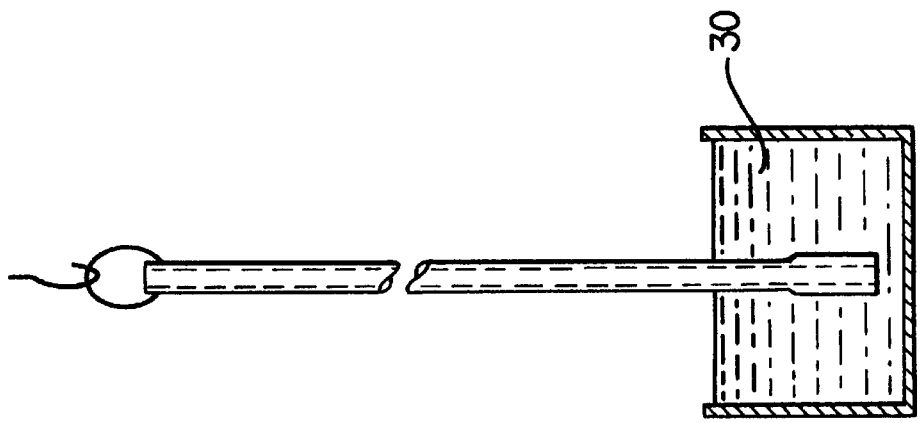
FIG. 3 are elevation views of different steps in carrying out the method of the present invention as employed in the manufacture of a catheter.
Figure 3B:
Figure 3C:
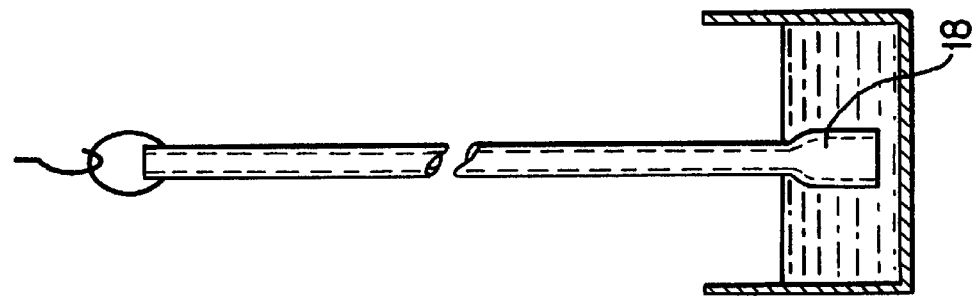
Figure 3D:
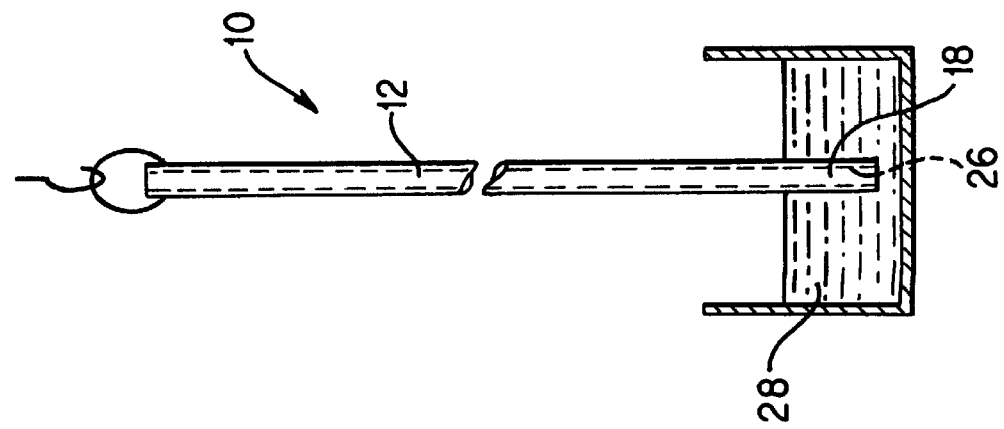

As shown in FIGS. 3a–3d, the tip end portion 18 of catheter 10 (with distal orifice 26), is preferably immersed in bath 28 as shown in FIG. 3a, contacting the tip end portion 18 of the tube 12 with a solution which includes a swelling agent, preferably a solvent, and a plasticizer. In response to the swelling agent, tip end portion 18 preferably swells to a diameter 10% to 300% in excess of its original diameter as is shown in FIG. 3b. As tip end portion 18 swells by reason of the action of the swelling agent, plasticizer is simultaneously carried into the polymeric catheter. The catheter tip end portion 18 is immersed in the plasticizing solution for a period of time sufficient to soften tip end portion 18 to the desired degree. For example, for catheters having a wall thickness less than 0.020 inches (0.0508 cm), adequate immersion times range from 1 to 30 minutes. The catheter is then removed from the bath and the swelling agent is evaporated-off by exposure to ambient air for a period of days, evacuation at room temperature and/or exposure of the catheter tip to hot air, as shown in FIG. 3c. Prior to being evaporated-off, the tip may be neutralized in bath 30 as shown in FIG. 3d, with an appropriate neutralizing agent. After evaporation and/or neutralization of the swelling agent, the catheter diameter shrinks. Depending on the amount of plasticizer that has entered or been absorbed by the polymeric material, however, the diameter of the catheter portion may not completely return to its original dimensions.

FIGS. 4a–4c shows an alternative method of making the catheter in accordance with the present invention. In FIG. 4a, tip end portion 18 of catheter 10 is immersed in a bath 32 comprising only the swelling agent. Tip end portion 18 is immersed in the swelling agent for a selected period time allowing the tip portion 18 to swell to the desired degree. Catheter 10 is then removed from the swelling agent bath and, as shown in FIG. 4b, tip end portion 18 is then immersed in a bath 34 comprising the plasticizer. The tip portion 18 remains immersed in the plasticizer bath for a period of time so as to sufficiently soften tip end portion 18 to the desired degree. After removal from the plasticizer, catheter 10 may be dried in the manner described above.

Figure 5A:
FIG. 5 shows further steps which may be employed in the method of the present invention, as utilized in the manufacture of a catheter.
Figure 5B:
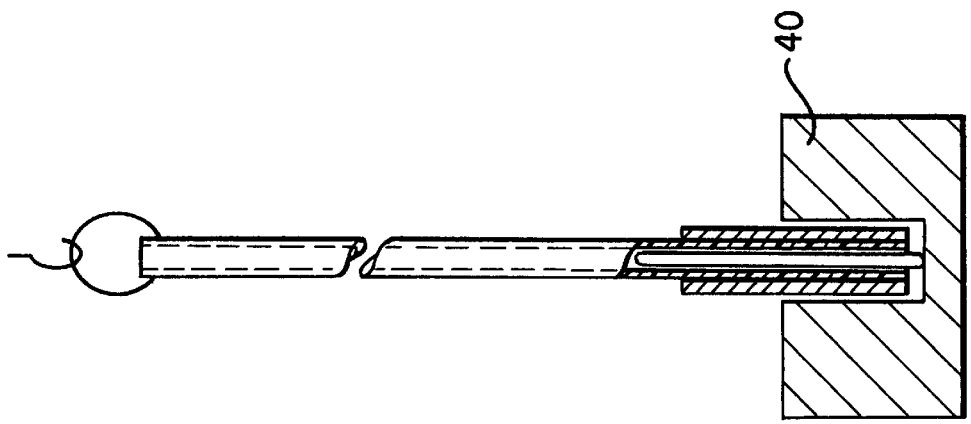
Figure 5C:
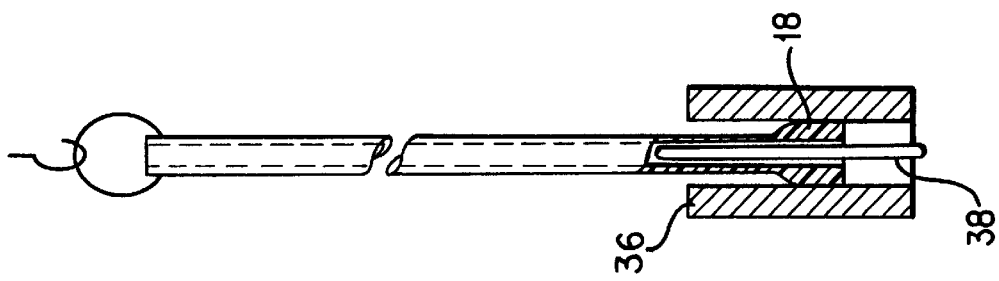

Once the plasticized catheter has been allowed to dry, the tip end portion may, if necessary, be conformed to its original or required outer dimension by surface grinding the swollen section on a centerless grinder or the like. Similarly, the catheter can be conformed to its original dimensions, or to any other dimension, or geometry, if so desired, by thermoforming means. One preferred technique of thermoforming is shown in FIGS. 5a, b and c. As shown there, a heat shrink tube, such as Teflon, or preferably a Freon TF swollen silicone rubber tube 36, whose preswollen inner diameter is that of the desired final outer diameter of the catheter, is placed over the swollen tip end portion 18 as shown in FIG. 5a using a mandrel 38 in the lumen of the catheter 10. The catheter is then heated in the vicinity of the swollen area by placing tip portion 18 in hot block 40 at an appropriate temperature to evaporate-off the swelling agent in the silicone rubber, and thus return it to its original dimensions or to shrink the heat shrink band (FIG. 5b). The shrinking portion of the tube or band compresses the tip end to its desired dimension, which it retains by action of the heat. FIG. 5c shows the completed catheter after removal of the silicone rubber forming tube. It should be understood that this thermoforming step can also be performed in conjunction with removing the swelling agent from the catheter.

Turning now to a more detailed description of the present invention in the preferred embodiment, the elongated fuseless polymeric tube is preferably made of extrudable or otherwise formable polymers such as polyamides and polyurethanes. The preferred polyamide materials include Nylon 6, Nylon 6/6, Nylon 6/9, Nylon 6/10, Nylon 9, Nylon 11, Nylon 12 and other available Nylons, such as Novolon (Nylon 11) material front Novoste Corporation, Aguadilla, Puerto Rico. Also included with the polyamide are blends or copolymers of polyamide with polyether or polyesters, with radiopaque fillers or the like, to provide thermoplastic elastomers of polyamides.

Where the polymeric tube is made of polyurethane, the preferred polyurethanes include those synthesized from the reaction products of macroglycols, macroglycols that are amine terminated, diisocyanates and chain extenders. Examples of suitable macroglycols include polyetherdiols, such as polytetramethylene glycol, polypropylene glycols, etc., polyesterdiols, polycarbonatediols, aliphaticdiols, etherlessdiols and the like. Suitable diisocyanates include 1,4-methylenebisphenyl diisocyanate (MDI), toluene diisocyanate, 1,4-methylene biscyclohexane diisocyanate (HMDI) or hydrogenated methylenebisphenyl diisocyanate, isophorone diisocyanate, linear 1,6-hexamethylene diisocyanate, and the like. Suitable chain extenders include aliphatic diols and diamines such 1,4-butanediol, 1,6-hexanediol, ethylenediamine, methylene dianiline, 1,4-cyclohexanediamine and the like and combinations of the above. Although the above reactants form linear, thermoforming polyurethanes or polyureas or combinations thereof, the invention also can be applied to thermosetting polyurethanes and polyamides made by incorporating reactants with hydroxyl or isocyanate functionality greater than 2.

As described above, the polymeric tube 12 is precision extruded or otherwise formed of the desired dimensions, length, inside and outside diameters and wall thickness for the particular desired applications. By way of illustration only, a typical angiographic catheter of the type described herein will be made of a tube so as to form a catheter having a French size of from about No. 2 to about No. 9. For such a catheter, the wall of the tube should be as thin as possible (and the inside diameter as large as possible) to permit high fluid flow rates or passage of therapeutic devices while maintaining the necessary strength and stiffness in the body portion of the tube. Such a catheter may have a wall thickness from about 0.007 to about 0.015 inches (0.017 cm to 0.0381 cm), although a range from 0.002 to 0.020 inches (0.005 to 0.0508 cm) may also be employed.

Following formation of the polymeric tube 12, and the solid state polymerization described in U.S. Pat. No. 4,963,306, the portion of the tube which will comprise the tip end portion 18 or a part of said tip end portion of the catheter is contacted with a swelling agent/plasticizer solution. As noted above, the solution preferably comprises a swelling agent and a plasticizer. The swelling agent is selected to cause the polymeric material of the tube 12 to expand or swell, thereby allowing the plasticizer to migrate, imbibe, absorb, diffuse or seep into the polymeric material. Also, the swelling agent can act as a carrier, where the combination of swelling agent and plasticizer swells the polymer to a greater extent than just the swelling agent alone.

The swelling agent selected should be a swelling agent suitable for the particular polymeric material, either polyamide or polyurethane, and for the plasticizer used. In particular, the swelling agent should have a strength or concentration sufficient to cause the polymeric material to expand, but without significantly weakening or destroying the polymeric material. The swelling agent is preferably a material which, when exposed to the polymer at a selected temperature (usually a temperature lower than that at which the polymeric material will dissolve) causes swelling of the polymer rather than dissolution or etching of the polymer. The swelling agent should also be capable of being removed from the polymer after the plasticizer is in place with subsequent shrinkage of the polymer and entrapment of plasticizer. And finally, the swelling agent is preferably capable of swelling the polymer at least about 10% to a maximum of about 300% to enable fast and thus economical uptake of plasticizer into the polymer.

Examples of swelling agents for the preferred polyamide material include formic acid, acetic acid, cresols, phenols, chromic acid and the like, applied at a temperature lower than that at which dissolution or significant damage of the polymer may occur. For example, formic acid has been found to work well with the polyamide material described above to expand the material sufficiently without significantly weakening the polyamide. Especially good results for polyamide have been obtained using a solvent concentration of 88% formic acid (available from Fisher Scientific), although more dilute or more concentrated formic acid may also be used depending upon the thickness of the polymeric tube and the solution temperature. A preferred temperature for swelling Nylon 11 and 12 is formic acid at about 45° C. At this temperature, nylon 11 and 12 reversibly swell approximately 10%–30% larger than its original size. Nylon 11 and 12 tend to dissolve in formic acid at temperatures greater than 100° C.

Examples of swelling agents for polyurethanes are methylene chloride, 1,1,1-thrichloroethane, methylethyl-ketone and the like. As with the polyamides, these solvents may dissolve polyurethane at higher temperatures. However, when the temperature is maintained below the temperature where dissolution may occur, the polyurethane will swell but will not dissolve. A preferred swelling agent for polyurethane is methylene chloride at room temperature. Catheter samples comprised of polyurethanes will swell from 10% to 300% when exposed to this swelling agent for a sufficient amount of time.

With respect to the plasticizer, the preferred plasticizer is one that is capable of being combined with the selected swelling agent (in solution) and must also be compatible with the polymeric material of the tube. Also desirable is that the plasticizer be of sufficient molecular weight and chemical composition such as to resist leaching out, or evaporating out of the polymeric material when used in its intended physiological environment.

Such plasticizers for polyamides include aromatic and aliphatic sulfonamides, such as N-butylbenzene sulfonamide, N-hexylbenzenesulfonamide, N-decylbenzenesulfonamide, N-cyclohexylbenzylsulfonamide, toluene derivatives of the above such as p-toluenesulfonamide, N-ethyl-p-toluenesulfonamide, N-butyl-p-toluenesolfonamide, N-hexyl-p-toluenesulfonamide, N-decyl-p-toluenesulfonamide, N-cyclohexyl-p-toluenesulfonamide; N-alkyl aliphaticsulfonamides; orthophosphates, such as monooctyl diphenyl phosphate, cresyl phenyl phosphate and xylenyl diphenyl phosphate; esters of aliphatic carboxylic acids, such as dioctyl azelate and dioctyl sebacate; lactams; lactones; cyclic ketones; adducts of oxycarboxylic acids with alkylene oxides; amylcyclohexanol carbonate and tetrahydrofurfuryl carbonates; chlorinated aromatic hydrocarbons and ethers thereof; adducts of polyamides with ethylene oxide; condensates of urethanes and formaldehydes; condensates of isocyanates and polyoxy compounds; and amorphous polyamides.

Such plasticizers for polyurethane include any of its reactants, for example, polyether glycols, polyester diols, such as dibutyldiglycol adipate, caprolactam, castor oil, polycarbonate oligomers, monooctyl diphenyl phosphate, aliphatic diols, aliphatic amines; aromatic and aliphatic sulfonamides such as N-butylbenzene sulfonamide, N-hexylbenzenesulfonamide, N-decylbenzenesulfonamide, N-cyclohexylbenzylsulfonamide, toluene derivatives of the above such as p-toluene-sulfonamide, N-ethyl-p-toluenesulfonamide, N-butyl-p-toluenesolfonamide, N-hexyl-p-toluenesulfonamide, N-decyl-p-toluenesulfonamide, N-cyclohexyl-p-toluenesulfonamide; N-alkyl aliphaticsulfonamides and the like.

In general, where the plasticizer is combined with the swelling agent in a solution, the solution may comprise variable amounts of swelling agent and plasticizer, including between 10%–98% swelling agent and 2%–90% of the plasticizer, depending, in part, on the strength of the swelling agent, the processing time permitted and the thickness of the polymeric tube 12. Preferably, between 50%–90% of the swelling agent and 10%–50% of the plasticizer may be employed. It can be expected that less swelling agent will be required when a more concentrated form is used. Conversely, when a weaker (less concentrated) swelling agent is used, the solution may comprise more of the swelling agent component and a longer immersion or dwell period may be required.

For manufacture of the preferred polyamide thin-wall catheter, the preferred plasticizers for quick imbibition or adsorption into the polyamide material are N-butylbenzenesulfonamide and N-hexyl-benzenesulfonamide. These plasticizers are soluble in formic acid, the preferred swelling agent for Nylon 11 and 12. When the preferred solvent and plasticizer is used, the solution preferably comprises about ⅔ part of 88% formic acid to ⅓ part of sulfonamide plasticizer. Swelling solutions comprised of these mixtures of N-butylbenzenesulfonamide and formic acid swell Nylon 11 and 12 to diameters 60% larger than formic acid alone, as N-butylbenzenesulfonamide and N-hexylbenzenesulfonamide behave synergistically to achieve these high swelling percentages.

For thin-walled polyurethane catheters, these catheters are softened by immersing the catheter segment into a solution of 50/50 methylene chloride and N-butylbenzene sulfonamide (or N-hexylbenzenesulfonamide) at room temperature for approximately 10 minutes. The catheter section is swollen approximately 50% larger with this softening solution.

To even further speed the entry of plasticizer into the polymer, the solution is preferably maintained at a temperature at or above normal room temperature but not so high as to significantly cause the polymer to dissolve or the swelling agent to significantly evaporate-off. For the preferred polyamide polymer, solvent and plasticizer, a bath temperature of about 45° C. is preferred, although this may be varied, depending on the tube thickness and solvent strength. For making a thin-walled angiographic catheter, the tip of the tube or catheter is immersed in the preferred solution for approximately 3 to 12 minutes. For the preferred polyurethane catheter, swelling agent and plasticizer, the preferred temperature is room temperature and the preferred time is approximately 10 minutes.

As noted above, time and temperature requirements may be adjusted depending on the wall thickness of the polymeric tube and the concentration of solvent. For example, polymeric tubes having a wall thickness greater than the preferred range of 0.004–0.015 inches (0.0101 to 0.0381 cm) for angiographic catheters may require a longer dwell time and/or an increased temperature. Similarly, if the solution is at a lower temperature, such as room temperature, a longer immersion time would be required to effect the addition of plasticizer to the polymeric material of the tip portion. The tip may be contacted with solution in several different ways but is preferably contacted by directly immersing or dipping the tip portion into a solution bath. Other techniques which may also work include spraying or wiping. Typically, only the most distal portion of the tip, such as the last one-half (½) inch (approximately 1.27 cm), is contacted with the solution, although the entire tip end portion or mid-distal end portion could also be contacted without departing from the present invention.

After removal of the tube or catheter tip from the solvent/plasticizer solution, the catheter or tube, if subjected to an acidic solution, such as formic acid and N-butylbenzenesulfonamide, is preferably subjected to a neutralization step to neutralize any residual formic acid swelling agent. Air neutralization or evaporation may be employed. Preferably, however, the catheter or tube is neutralized by contacting the tip with an alkaline solution having a buffered or non-buffered pH of 7 or greater. In the preferred embodiment, the tip portion is immersed or dipped into a solution of ammonia having a pH of approximately 10 and allowed to dwell in the neutralizing solution for several minutes.

As a final step, the polymeric tube may be dried in open air for a period of time to allow any remaining solvents to evaporate. It has been found that a drying period of approximately two (2) days at room temperature is sufficient. The drying time can be accelerated, however, by heating the catheter. Temperatures of 60° C. for thirty minutes are sufficient to effectively flash off remaining swelling agent.

Following drying, tip end portion 18 may be ground to remove any remaining swelling and/or to form a tapered or manicured configuration. Similarly, as described above, the swollen catheter tip may be thermoformed with shrink tubing (with a mandrel in its lumen) to provide a desired wall thickness and inner and outer diameter. A desired curvature may also be imparted to the mid-distal and/or tip end portion, depending upon the procedure for which the catheter is to be employed. In accordance with well-known thermosetting technique, the catheter tip is formed into the desired shape (as by inserting the tip over a mandrel or wire form of a desired shape) and by dipping the tip into hot water for a short period of time to set the shape of the tip. Such a technique is also disclosed in U.S. Pat. No. 4,963,306.

FIG. 6 shows another embodiment of the catheter of the present invention. This catheter includes an elongated fuseless polymeric tube 12 which also has a body portion 14 and a tip portion 18 which includes a "pig tail" curvature.

In this embodiment, essentially the entire distal portion 15 is contacted with the solvent/plasticizer solution described above, preferably by dipping for approximately two (2) minutes. The mid-distal portion is withdrawn from the solution and approximately two (2) centimeters of the most distal tip end portion 18 are then contacted (allowed to remain in the solvent/plasticizer for an additional five to ten minutes. Usually this process is performed prior to formation of the pig tail curvature. This results in a distal end portion itself having parts with different amounts of plasticizer, the tip end portion 18 having the greatest amount of plasticizer and being the most pliable or flexible. Neutralizing and drying steps discussed above may also be performed.

To obtain the so-called "pig tail" curl, the polymeric tube is placed on an inner mandrel 42 having the pig tail configuration shown in FIG. 6. The curled mandrel 42 with attached tube 12 are immersed in hot water or other solution, including hot air, which acts to relieve internal stresses set the shape of the tip to conform to that of the mandrel, in a manner well known in the art.

Without implying any limitation to the present invention, the following examples are offered for illustrative purposes only:

EXAMPLE 1

Example of making the plasticizer

N-Hexylbenzenesulfonamide was made in the following manner: Pyridine (7.91 g) was mixed with 1-hexylamine (10.12 g) and cooled in an ice bath. Benzenesulfonylchloride (10.12 g) was then slowly dripped into this cooled solution with continuous stirring of the exotherming reaction. This solution was dissolved in 100 ml methylene chloride, and washed with equal amounts of distilled water in a separatory flask. The upper eluent was discarded and the wash repeated three times with 1 molar hydrochloric acid, once with 2% sodium bicarbonate and again with saturated sodium chloride solution. After proper separation, the lower product containing solution was transferred to a beaker and heated to evaporate-off the methylene chloride leaving the product, N-hexylbenzenesulfonamide which was stored in a bottle until used.

EXAMPLE 2

Example of making the plasticizer

N-Decylbenzenesulfonamide was prepared in the same manner as Example 1, however, 15.73 g of 1-decylamine was used instead of 1-hexylamine.

EXAMPLE 3

Nylon 11 catheter tubing is extruded in a conventional manner with a French 7 outer diameter (0.222 cm) and a 0.007 inch (0.017 cm) wall. A 100 cm length of this tubing is placed over a wire mandrel and the distal 5 cm is immersed in flowing cold water and the remaining portion of the catheter is exposed to hot air (140° C.) for 30 minutes. The catheter is removed from the oven and water and the distal 0.4 cm of the resultant two zone catheter is then dipped in a warm solution (40–45° C.) of 33% N-butylbenzenesulfonamide (Plastohall BSA, from C. P. Hall, Co.) in 88% pure formic acid (Fisher Scientific) for 8 minutes at which point the catheter tip swells approximately 10%–30%. The resultant three-hardness zone catheter is then removed from this solution and dipped into a solution of 1% ammonium hydroxide for 5 minutes to neutralize residual formic acid. The catheter is then dried at 50° C. for one hour. (It could also be dried at room temperature for about two days.) The outer diameter of the catheter is then ground to provide a slight taper toward the tip.

EXAMPLE 4

A Shore 75D hardness polyurethane catheter tube is extruded in a conventional manner with a French 7 outer diameter (0.222 cm) and a 0.007 inch (0.017 cm) wall. A 100 cm length of this tubing is placed over a wire mandrel and the distal 0.4 cm tip is dipped in a room temperature solution of 50% N-hexylbenzenesulfonamide (from example 1) in methylene chloride (Fisher Scientific) for 12 minutes at which point the catheter tip swells approximately 50%. The resultant two-hardness zone catheter is then removed from this solution and a 2 cm section of preswollen, in Freon TF, silicone rubber tubing (0.222 cm, ID. 0.300 cm wall), is placed over the swollen polyurethane area and the distal 1 cm portion heated in a shallow hole in a temperature controlled hot plate (100° C.) for 5 minutes. Heating caused the swollen catheter tip to flow back to its original French 7 diameter with 0.007 inch (0.017 cm) wall. The tip hardness was measured as Shore 70A.

EXAMPLE 5

The most distal 8 cm of the inner member component and the most distal 2 cm of the outer member component and the nylon balloon component of a Nylon 12 angioplasty multi-lumen balloon catheter (wherein a guidewire passageway is defined within the inner member and a balloon inflation passageway is defined between the inner and outer members) were dipped into a solution of 33% N-butylbenzenesulfonamide in formic acid for 10 minutes, removed, neutralized and dried, as in Example 3 above. The softened inner and outer member sections were stretched and clamped over an inner mandrel and heated to 110° C. for 10 minutes to thermoform the softened sections back to its original diameters. The inner and outer members and balloon were then assembled into an angioplasty multi-lumen balloon catheter wherein the distal section was soft and flexible and the nylon balloon section and balloon legs or ends were soft and easy to pull down for insertion into a small diameter guiding catheter.

EXAMPLE 6

The most distal 10 cm of a polyurethane catheter, similar to the one described in Example 4, as exposed to a solution of 50% castor oil in methylene chloride for one hour. The most distal 0.4 cm was then immersed in a solution of 50% N-decylbenzenesulfonamide, from Example 2, for an additional 10 minutes. The resultant catheter was dried in an oven at 50° C. for one hour, rinsed in methylene chloride for 5 seconds to remove surface plasticizer and the tip centerless ground to its original diameter. The resultant three-zone catheter had a Shore 75D proximal end, a Shore 55D mid-distal end and a Shore 80A most distal atraumatic tip.

EXAMPLE 7

The distal 0.4 cm tip of a 10 cm long section of Shore Hardness 90A polyurethane tubing was immersed in a bath containing 50% N-hexylbenzenesulfonamide in methylethyl ketone for 10 minutes. The catheter was removed and the methylethyl ketone was evaporated-off in room air overnight. The 10 cm length, with the softened 0.4 cm tip, which measured Shore 60A in durometer, was then fused to a Shore 55D polyurethane tube to provide a three zone catheter with an atraumatic tip.

The foregoing description and examples are for purposes of illustration and not limitation, and the scope of the present invention is defined by the appended claims. Although the present invention has been described most specifically in connection with making a catheter having a distal end portion of different degrees of flexibility, the present invention also has other applications such as application in the manufacture of balloons for balloon angioplasty catheters. Balloon angioplasty catheters are typically inserted through the lumen of a guiding catheter located within the vascular system of a patient and extending to the proximity of the blockage site. It is normally desirable to use the smallest possible diameter guiding catheter.

However, one difficulty sometimes experienced is that upon deflation, the balloon does not deflate to a lay-flat position along the catheter. As a result, the balloon will, on occasion, make it difficult to withdraw the angioplasty catheter through the guiding catheter. When this occurs, both guiding and angioplasty catheters must be withdrawn, even though it is often medically preferable to allow the guiding catheter to remain in place for subsequent procedures and to reduce any risk associated with vascular collapse. Treatment of the balloon with the method described above (i.e., contacting it with a swelling agent and a plasticizer) to soften the balloon is believed to provide enhanced properties which will result in a more complete collapse of the balloon upon deflation, and allow withdrawal of the angioplasty catheter through the smallest possible guiding catheter.

This is but one example of further application of the present invention in addition to those described in more detail above. For these reasons, the present invention is not limited to the specific embodiments described in this specification, but is defined according to the appended claims.

What is claimed is:

1. A plastic article of polyamide at least a portion of which has been contacted with a swelling agent and a plasticizer to render said portion softer or more pliable than the portion of said plastic article which has not been contacted with said swelling agent and said plasticizer, said swelling agent selected from the group consisting of formic acid, acetic acid, cresols, phenols, and chromic acid so as to swell said portion contacted with said swelling agent from about 10% to about 300%.

2. The article of claim 1 said portion having been contacted with a solution comprising said swelling agent and said plasticizer.

3. The article of claim 2 wherein said solution comprises approximately $2/3$ part formic acid and approximately $1/3$ part N-butylbenzenesulfonamide, the temperature of said solution being greater than room temperature and less than the temperature at which formic acid dissolves said polyamide during the time contacted and said first portion having been contacted with said solution by immersing said first portion in said solution.

4. The article of claim 1 wherein said swelling agent comprises formic acid and said plasticizer comprises a plasticizer selected from the group consisting of N-butylbenzenesulfonamide and N-hexylbenzenesulfonamide.

* * * * *